(12) United States Patent
Doble

(10) Patent No.: US 6,364,891 B1
(45) Date of Patent: Apr. 2, 2002

(54) BACK BITING SURGICAL INSTRUMENT

(76) Inventor: Peter Doble, 3399 Willon Way, Twin Falls, ID (US) 83308

( * ) Notice: Subject to any disclaimer, the term of this patent is extended or adjusted under 35 U.S.C. 154(b) by 0 days.

(21) Appl. No.: 09/663,229

(22) Filed: Sep. 15, 2000

Related U.S. Application Data

(62) Division of application No. 09/446,258, filed as application No. PCT/US98/18075 on Aug. 31, 1998, now Pat. No. 6,280,459.
(60) Provisional application No. 60/057,467, filed on Sep. 3, 1997.

(51) Int. Cl.⁷ ................................. A61B 17/14
(52) U.S. Cl. ....................... 606/184; 606/207
(58) Field of Search ................ 606/205–208, 606/170, 174, 184, 176, 210, 211, 185

(56) References Cited

U.S. PATENT DOCUMENTS

| | | | | |
|---|---|---|---|---|
| 5,569,299 A | * | 10/1996 | Dill et al. | 606/207 |
| 5,571,131 A | * | 11/1996 | Ek et al. | 606/167 |
| 5,618,306 A | * | 4/1997 | Roth et al. | 606/205 |
| 5,683,359 A | * | 11/1997 | Farkas et al. | 606/170 |

\* cited by examiner

Primary Examiner—Kevin Truong

(57) ABSTRACT

A surgical instrument is provided for cutting tissue. The surgical instrument includes a shaft having proximal and distal ends, a cutter coupled to the distal end, and a handle coupled to the proximal end. The cutter is formed to include a base having two cutting edges providing an opening, a slider, and a tip coupled to both the base and the slider. The cutter is formed to move between a fully open position in which the cutting edges of the tip form an obtuse angle relative to the shaft and a fully closed position in which the tip is received within the opening of the base. The handle is arranged to move the cutter between the open and closed positions.

10 Claims, 6 Drawing Sheets

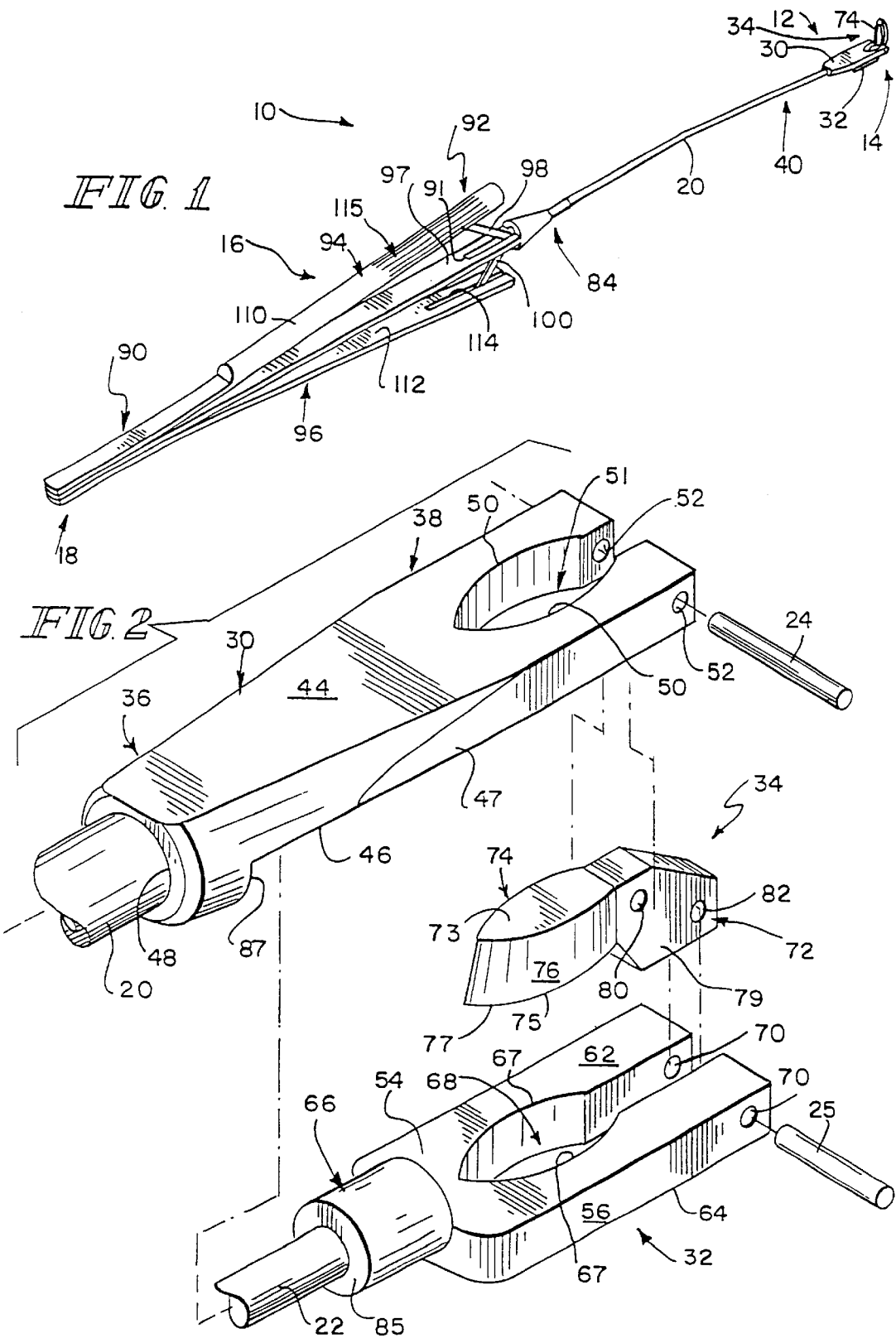

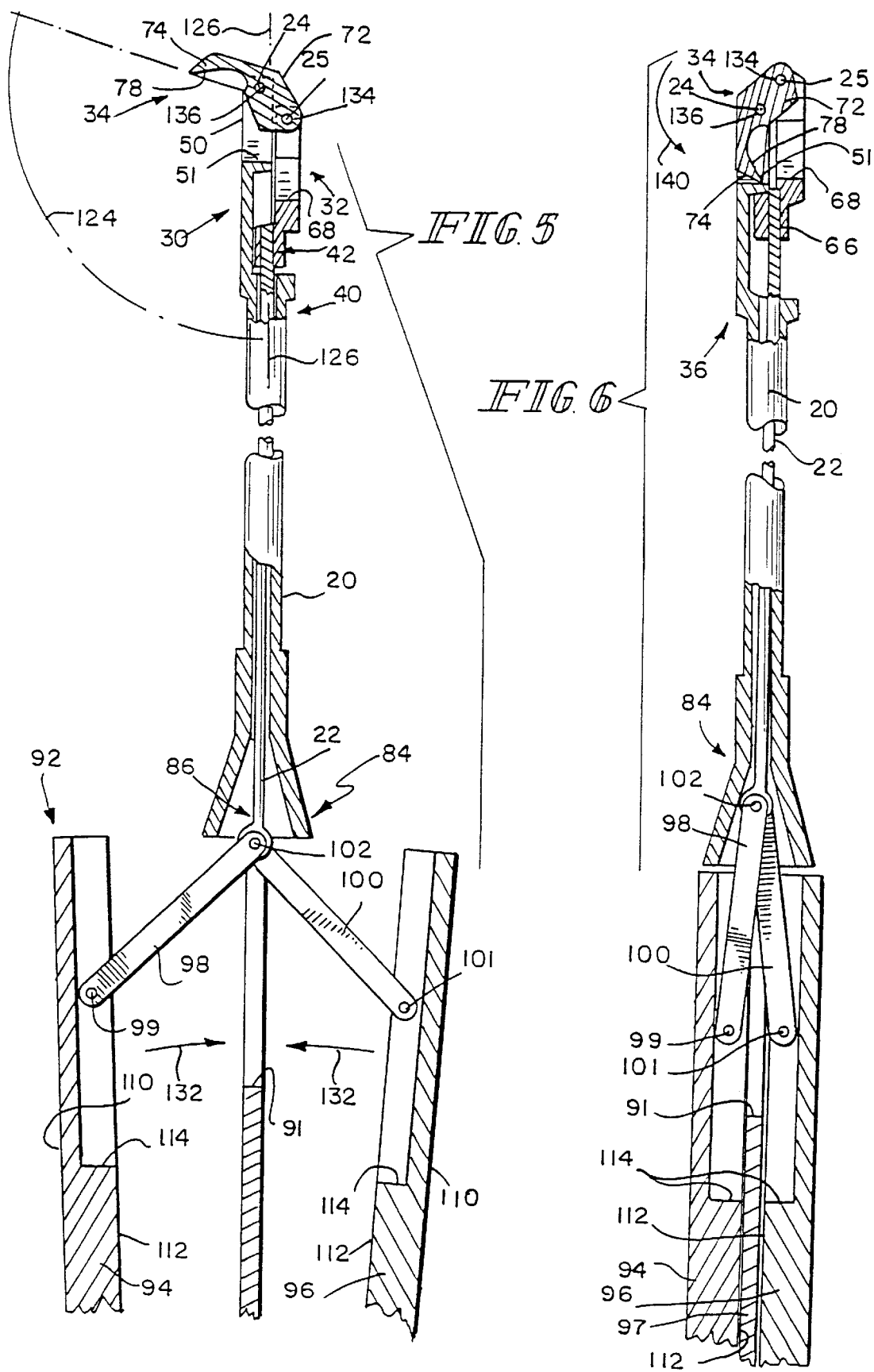

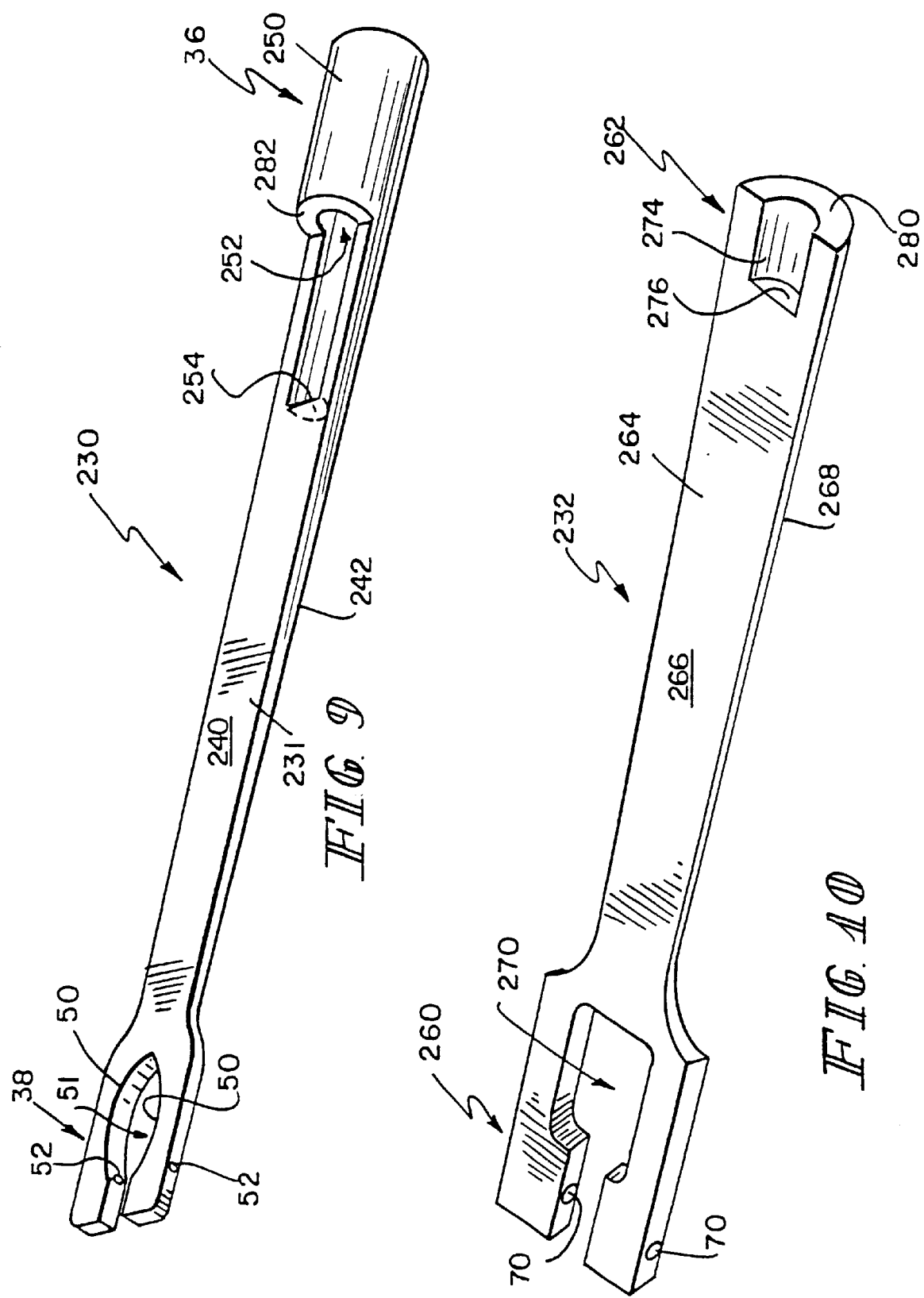

US 6,364,891 B1

BACK BITING SURGICAL INSTRUMENT

BACKGROUND AND SUMMARY OF THE INVENTION

This application is a divisional application of U.S. patent application Ser. No. 09/446,258, filed on Dec. 20, 1999, now U.S. Pat. No. 6,280,459 which is a 571 of PCT/US98/18075 filed Aug. 31, 1998 U.S. Pat. No. 6,280,459 which is a provisional of 60/057,467 filed Sep. 3, 1997.

The present invention relates to surgical instruments, and particularly to surgical instruments used in minimally invasive endoscopic transitional space surgeries or other endoscopic procedures. More particularly, the present invention relates to a surgical instrument used for cutting tissue.

During most minimally invasive surgeries of the sinuses, knee, shoulder, and other joints, a smaller surgical instrument is preferred. A number of instruments have been developed, including those shown in U.S. Pat. Nos. 5,443, 475 and 4,977,900, for such surgeries. The disclosure of these U.S. Pat. Nos. 5,443,457 and 4,977,900 are incorporated herein by reference for purposes of combining techniques and concepts. Instruments such as those shown in these referenced patents are typically used with an endoscope which allows the surgeon to view the interior of the area under repair through an eye piece or, alternatively, on a video display screen.

An initial process in many minimally invasive endoscopic transitional space (sinus) surgeries is cutting the uncinate process. The uncinate process is an obstructive piece of cartilage and is cut for the purpose of exposing the ostium, which leads into the maxillary sinus cavity. A large degree of precision, maneuverability, and control is needed in order to effectively cut the uncinate process and many other tissues in endoscopic surgeries.

According to the present invention, a surgical instrument is provided for cutting tissue. The instrument includes a shaft having distal and proximal ends and a cutter coupled to the distal end of the shaft. The cutter is formed to include a base, a slider positioned to lie adjacent to the base, and a tip coupled to the base and the slider. The base is formed to include an aperture providing two cutting edges and the tip is also formed to include two corresponding cutting edges for cooperation with the cutting edges of the base. The cutter is formed to move between a fully open position in which the cutting edges of the tip form an obtuse angle relative to the shaft to a fully closed position in which the tip is received within the aperture of the base. The instrument is also formed to include a handle coupled to the proximal end of the shaft. The handle is arranged to move the cutter between open and closed positions.

In preferred embodiments, the handle is formed to include a right handle grip, a left handle grip, and a center beam positioned to lie between the right and left handle grips. The right and left handle grips are coupled to the center beam at a proximal end of the handle and are normally spaced-apart from the center beam at a distal end of the handle. In order to move the cutter to the fully closed position, the handle grips are squeezed toward the center beam in a direction transverse to an axis running through the shaft. The surgical instrument of the present invention is adapted to be held by the thumb and index finger, supported on the middle finger and actuated by squeezing the thumb and index finger together.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a back biting surgical instrument of the present invention showing a cutter for cutting tissue during an endoscopic procedure, a handle for moving the cutter between fully opened and fully closed positions, and a hollow shaft extending between the cutter and the handle;

FIG. 2 is an exploded perspective view of the cutter of the present invention showing a base having two curved cutting edges forming an opening, a slider also having two curved edges forming an opening, and a tip having a cutter head including two curved cutting surfaces adopted to cooperate with the cutting edges of the base to create a shearing motion;

FIG. 5 is a sectional view, with portions broken away, of the cutter in the fully opened position showing an obtuse angle formed between the lower surface of the cutter head and an axis running through a distal end of the shaft and also showing the handle including two handle grips, a link pivotally coupled to each handle grip and a rod received within the hollow shaft, and a center beam positioned to lie between each handle grip;

FIG. 6 is a sectional view similar to FIG. 5 showing the cutter in the fully closed position so that the handle grips are moved inward toward the center beam and the cutter head of the tip is received within the opening of the base;

FIG. 9 is a perspective view of the alternate base of FIG. 8 showing an elongated mid-section and a semi-circular portion with a cut-out section at a proximal end; and FIG. 10 is a perspective view of the alternate slider of FIG. 8 showing a rectangular shaped opening and a groove at a proximal end for receiving the rod.

DETAILED DESCRIPTION OF THE DRAWINGS

Figure 7:
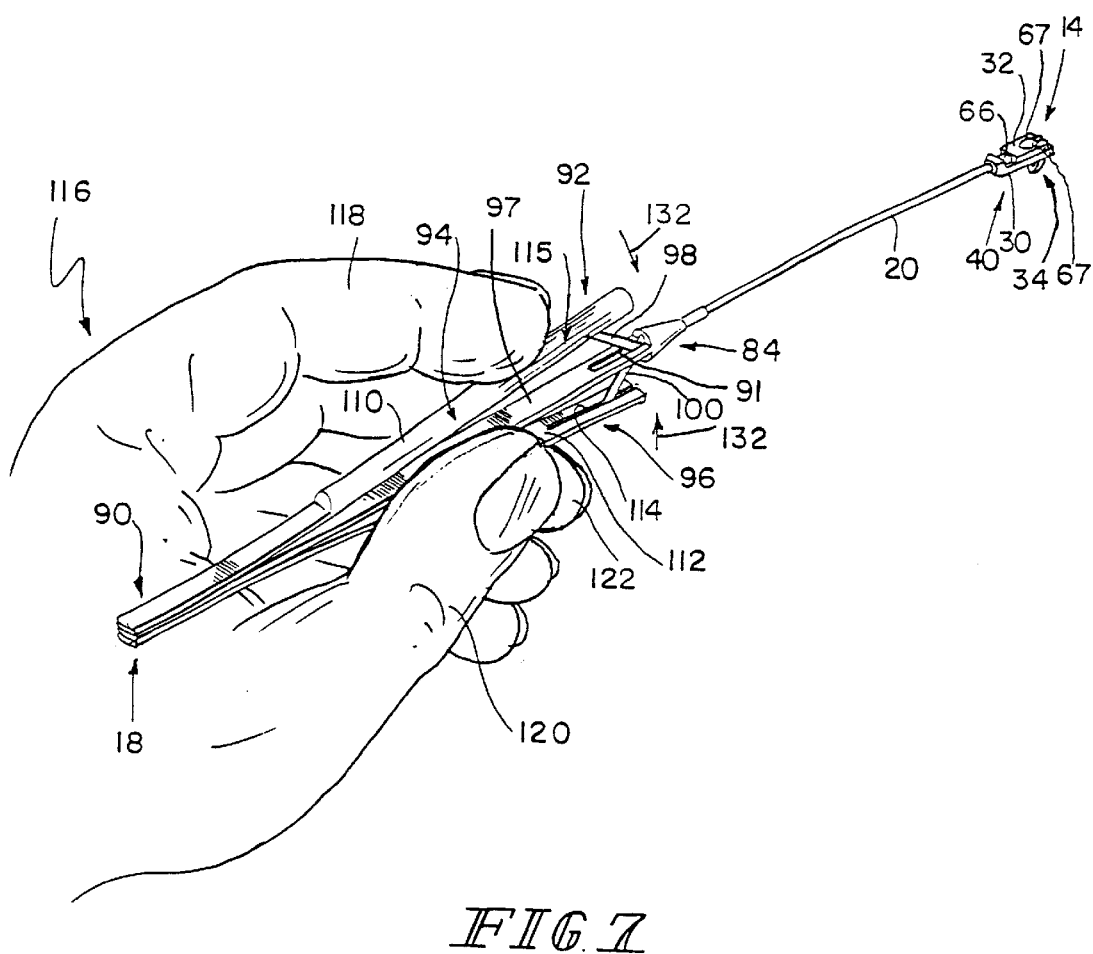
FIG. 7 is a perspective view of the surgical instrument of the present invention showing a hand grasping the handle of the present invention with a "pencil-like" grip for improved control and precision in operation.

A surgical instrument 10 is provided for use in minimally invasive endoscopic transitional space surgeries (sinus surgeries), but may be used for other endoscopic procedures as well. Instrument 10 is formed to include a cutter 12 located at a distal end 14, a handle 16 located at a proximal end 18, and a hollow shaft 20, and a rod 22 received within hollow shaft 20. The hollow shaft 20 and rod 22 each extend between cutter 12 and handle 16, as shown in FIG. 1. The cutter 12 is formed to move between a fully open position and a fully closed position through operation of the handle 16. Handle 16 is formed to be held by a surgeon or technician by using a "pencil-like" grip, as shown in FIG. 7.

Cutter 12 is formed to include a base 30, a slider 32, and a tip 34 coupled to both base 30 and slider 32, as shown by the dotted lines in FIG. 2. Base 30 is formed to include a proximal end 36 and a distal end 38. Proximal end 36 is coupled to a distal end 40 of shaft 20. Base 30 is also formed to include a top surface 44, a bottom surface 46, and side walls 47. Proximal end 36 of base 30 is formed to include a shaft-receiving aperture 48 and distal end 38 is formed to include two cutting edges 50 forming a tear-drop shaped opening 51 extending through distal end 38 of base 30. Apertures 52 are formed to extend through distal end 38 and are provided for receiving a first pin 24 in order to pivotally couple tip 34 with base 30.

Figure 3:
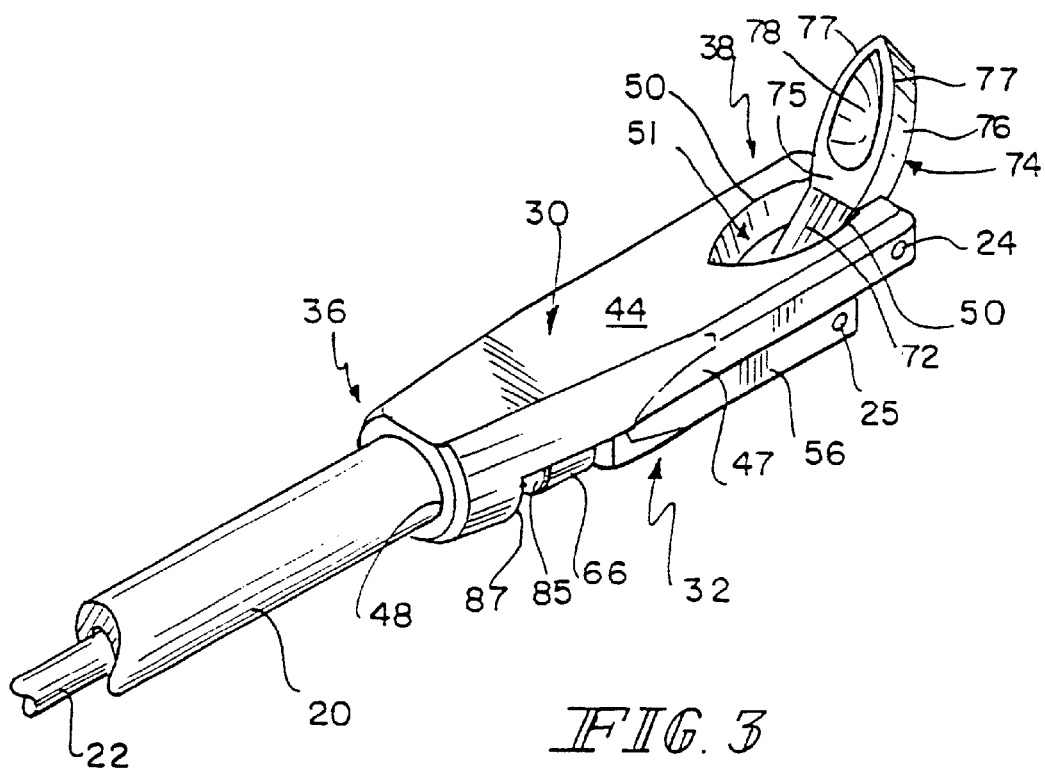
FIG. 3 is a perspective view of the cutter in the fully opened position showing the cutting edges of the cutter head, a recessed portion of a lower of the cutter head, and also showing the tip being pivotally coupled to each of the base and the slider.
Figure 4:
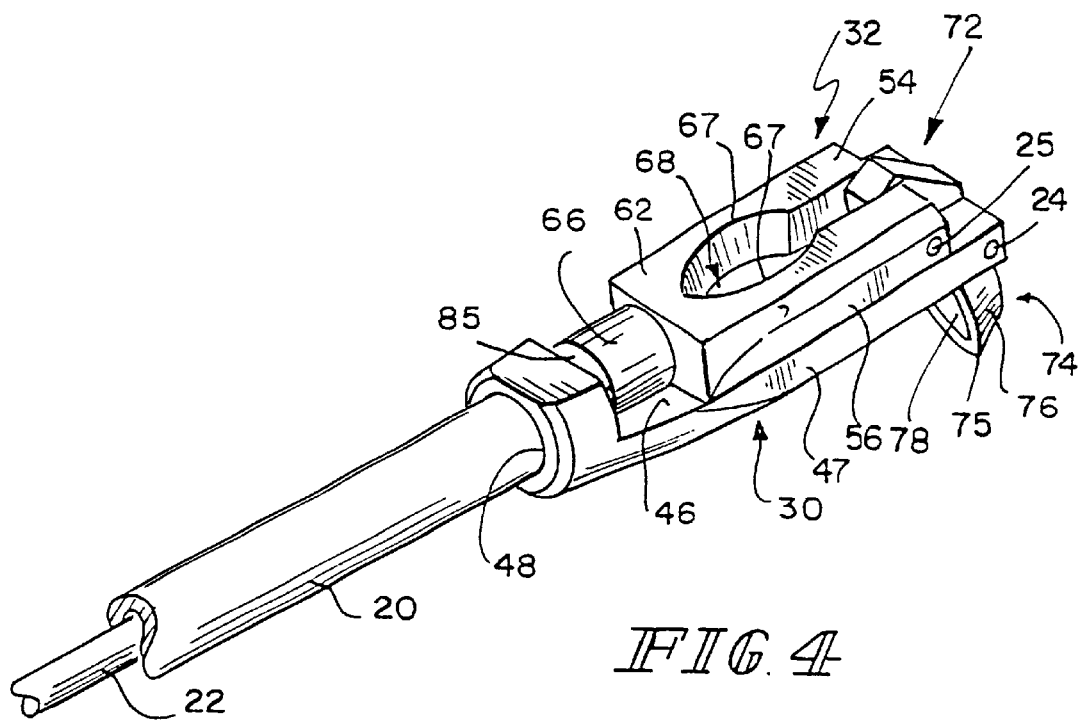
FIG. 4 is a perspective view a the backside of the cutter in the fully opened position showing the opening of the slider.

Slider 32 is formed to include a body 54 having side walls 56, a top surface 62, and a bottom surface 64 where side walls 56 extend between top and bottom surfaces 62, 64. Body 54 is also formed to include two curved edges 67 forming a tear-drop shaped opening 68 similar to opening 51 of base 30 and apertures 70 extending through body 54 and provided for receiving a second pin 25 in order to pivotally couple tip 34 with slider 32. Slider 32 is also formed to include a hollow cylinder 66 coupled to body 54 and formed for receiving a distal end 42 of rod 22. When fully assembled, top surface 62 of slider 32 is positioned to lie adjacent to and in engagement with bottom surface 46 of base 30, as shown in FIGS. 3 and 4.

Tip 34 is formed to include a pivot head 72 and a cutter head 74 extending from pivot head 72. Cutter head 74 is tear-drop shaped and is formed to include an upper surface 73, a lower surface 75, and two curved side surfaces 76 extending between upper and lower surfaces 73, 75. Two cutting edges 77, as shown in FIG. 3 define an outer perimeter of lower surface 75. Cutting edges 77 of cutter head 74 are formed to cooperate with cutting edges 50 of base 30. Lower surface 75 is also formed to include a recessed portion 78, also shown in FIG. 3. Pivot head 72 of tip 34 is formed to include two side walls 79, a first aperture 80 formed to extend between side walls 79, and a second aperture 82 also formed to extend between side walls 79. When assembled, pivot head 72 of tip 34 is received within opening 51 of base 30 so that first aperture 80 is positioned to align with apertures 52 of base 30 and second aperture 82 is positioned to align with apertures 70 of slider 32. Aperture 80 and apertures 52 receive first pin 24 therethrough in order to pivotally couple tip 34 to base 30. Aperture 82 and apertures 70 are formed to receive second pin 25 in order to pivotally couple tip 34 to slider 32.

Shaft 20 and rod 22 are each formed to include distal ends 40, 42, respectively, and a proximal end 84, 86, respectively, as shown in FIG. 7. Shaft 20 is hollow so that rod 22 is received within shaft 20 and is movable relative to shaft 20. Distal end 40 of shaft 20 is received within shaft-receiving aperture 48 of base 30. Proximal end 84 of shaft 20 is coupled to handle 16. Distal end 42 of rod 22 is received within cylinder 66 of slider 32. Similar to shaft 20, proximal end 86 of rod 22 is coupled to handle 16. In the fully open position, a lower surface 85 of hollow cylinder 66 of slider 32 is positioned to engage an upper surface 87 of proximal end 36 of base 30, as shown in FIG. 4. In the fully closed position, as shown in FIG. 6, lower surface 85 is spaced-apart from upper surface 87. Although base 30 and shaft 20 are shown and described as two separate members, it is within the scope of the present invention to manufacture base 30 and shaft 20 as one integral part (not shown). Slider 32 and rod 22 are also shown and described as two separate members, however, it is within the scope of the invention to also combine slider 32 and rod 22 to form one integral part (not shown).

Referring now to FIGS. 5, 6, and 7, handle 16 is formed to include a proximal end 90, a distal end 92, a left handle grip 94, a right handle grip 96, a center beam 97 positioned to lie between left and right handle grips 94, 96, and a first and second link 98, 100. Handle grips 94, 96 are each welded to center beam 97 at proximal end 90 and are spaced-apart from center beam 97 at distal end 92. It is within the scope of the present invention, however, to include any number of means of coupling each handle grip 94, 96 to center beam 97 at proximal end 90. Each handle grip 94, 96 is formed to include a curved outer surface 110 and a flat inner surface 112 positioned to face center beam 97. Flat inner surface 112 of each hand grip 94, 96 is formed to include an inner slit 114 at distal end 92. Inner slit 114 is formed to extend only partially through each handle grip 94, 96. Curved outer surface 110 of each handle grip 94, 96 is formed to include a splined portion 115 in order to make handle 16 easy for a user 116 to grasp, as shown in FIG. 7. Although splined portion 115 is shown, it is within the scope of the present invention to include handle grips 94, 96 having outer surface 110 including any type of knurled, textured, or ridged portion in order to increase the ease of use of the surgical instrument 10. Proximal end 84 of shaft 20 is coupled to center beam 97, as shown in FIG. 1. Shaft 20 and center beam 97 may also be manufactured as one integral part.

First link 98 is received within inner slit 114 of left handle grip 94 and is coupled therein at a pivot point 99. Second link 100 is similarly received within inner slit 114 of right handle grip 96 and is coupled therein at a pivot point 101. Each link 98, 100 is also coupled to proximal end 86 of rod 22 at a pivot point 102. Distal end 92 of center beam 97 is coupled to proximal end 84 of shaft 20, as shown in FIGS. 1 and 7. Distal end 92 of center beam 97 is also formed to include a cut-out portion 91 so that pivot point 102 is positioned to lie within cut-out portion 91. Cut-out portion 91 of center beam 97 also provides a space for links 98, 100 to move therein during operation.

Although handle 16 may be held in a number of ways, it is preferred for user 116 to grasp handle 16 with a "pencil-like" grip as shown in FIG. 7. With the pencil-like grip, an index finger 118 of user 116 is placed on the ridged portion 112 of either one of the handle grips 94, 96. A thumb 120 of the user is place in contact with the ridged portion 112 of the other handle grip 94, 96 so that surgical instrument 10 is supported between index finger 118 and thumb 120. A middle finger 122 of the user 116 is positioned to engage the same one of the handle grips 94, 96 which is supported by thumb 120 so that surgical instrument 10 may be better supported providing user 116 with increased control during surgical operations.

Cutter 12 may be moved between the fully open position, as shown in FIG. 5, in which an obtuse angle 124 is created between the lower surface 75 of cutter head 74 and an axis 126 running parallel to distal end 40 of shaft 20 and the fully closed position, as shown in FIG. 6, where cutter head 74 is received within opening 51 of base 30. In the fully closed position, inner surface 112 of each handle grip 94, 96 is positioned to lie adjacent to and in engagement with center beam 97. During the motion between the fully open position and the fully closed position, cutting edges 77 and side surfaces 76 of cutter head 74 are positioned to engage cutting edges 50 forming opening 51 within base 30, thus creating a shearing action between cutting edges 77 and surfaces 66 of cutter head 74 and cutting edges 50 of base 30. The two cutting edges cooperate with each other in order to form the shearing action.

In operation, user 116 holds handle 16 using the pencil-like grip described above. With index finger 118 and thumb 120, user 116 urges each handle grip 94, 96 inward in a direction 132, as shown by the arrows in FIG. 5. Left and right handle grips 94, 96 are urged to move toward center beam 97 until inner surface 112 of each handle grip 94, 96 is positioned to lie adjacent to and in engagement with center beam 97, as shown in FIG. 6. The handle 16 is thus operable in a "tweezer-like" fashion.

First and second links 98, 100 are coupled to respective handle grips 94, 96 at pivot points 99, 101 located within slits 114. As handle grips 94, 96 are urged in direction 132 toward center beam 97, first and second links 98, 100 are urged to pivot about pivot points 99, 101 so that first and second links 98, 100 are urged to move toward a generally upright or vertical position parallel to center beam 97. The inward and upward movement of links 98, 100 causes links 98, 100 to also pivot about pivot point 102 and thus move pivot point 102 upward as well. Because links 98, 100 are coupled to rod 22 at pivot point 102, rod 22 is also urged to move upward within shaft 20. During this motion, shaft 20 and beam 97 remain stationary relative to handle grips 94, 96, links 98, 100, and rod 22.

Distal end 42 of rod 22 is received within cylinder 66 of slider 32. Distal end 42 of rod 22 is thus coupled to slider 32 so that as rod 22 is moved upward, due to the inward, closing motion of handle grips 94, 96, rod 22 urges slider 30 in the same upward direction, as shown in FIG. 6. Slider 32 is coupled to cutter head 34 at a pivot point 134 by second pin 25. As slider 32 is moved upward, second pin 25 and pivot point 134 are also moved upward. As shown in FIG. 7, when cutter 12 is in the fully closed position, opening 68 of slider 32 is positioned to align with opening 51 of base 30 in order to allow cut tissue to pass therethrough.

Cutter head 34 is coupled to base 30 by first pin 24 at a pivot point 136. Because base 30 remains stationary as slider 32 moves upward relative to shaft 20, cutter 34 is urged to pivot about both pivot points 134, 136 causing cutter 34 to pivot in a downward direction, as shown by arrow 140 in FIG. 6. In the fully open position, as shown in FIG. 5, first pin 24 and pivot point 134 are positioned to lie generally above second pin 25 and corresponding pivot point 136. In the fully closed position, however, first pin 24 and pivot point 134 are positioned to lie generally below second pin 25 and pivot point 136. This is due to the upward motion of rod 22 causing pivot point 136 to move upward while pivot point 134 remains stationary with base 30.

As cutter 12 is moved toward the fully closed position, side surfaces 76 and cutting edges 77 of cutter head 74 are urged to pass through opening 51 formed by cooperating cutting edges 50 of base 30. As cutting edges 77 and side surfaces 76 of cutter head 74 pass through opening 51, a shearing action is created between the two cutting edges 77, 50. When used in surgery, for endoscopic surgical procedures such as sinus surgeries, this shearing action operates to cut away tissue from the surgical site. The cut tissue (not shown) is received within recessed portion 78 of cutter head 34. Because tear-drop shaped opening 68 of slider 32 is positioned to align with opening 51 of base 30 when cutter 12 is in the fully closed position, the tissue which is cut from the surgery site and received within recessed portion 78 is able to be passed through openings 51, 68 for disposal in order to avoid the clogging of instrument 10 with tissues and debris.

Figure 8:
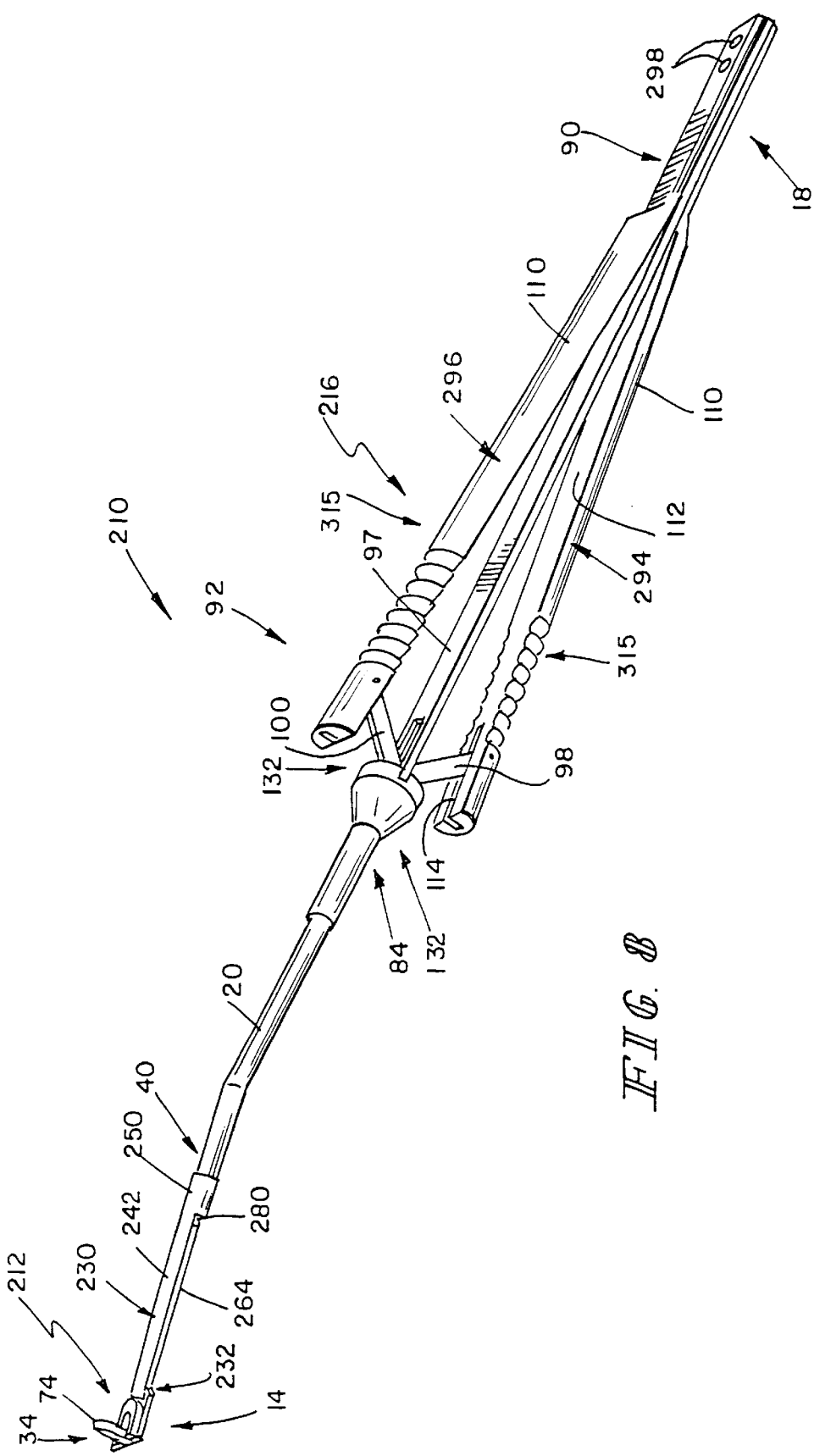
FIG. 8 is a perspective view of a preferred embodiment of the surgical instrument of the present invention showing an alternate base and slider and also showing the handle grips having a ridged portion.

Referring now to FIGS. 8–10, an alternate surgical instrument 210 is provided. Instrument 210 is formed to include a cutter 212 located at distal end 14, a handle 216 located at proximal end 18, hollow shaft 20, and a rod 22 received within hollow shaft 20. Instrument 210 operates in the a similar manner as instrument 10.

Cutter 212 is formed to include an alternate base 230, an alternate slider 232, and tip 34. As shown in FIG. 9, base 230 includes proximal end 36 and distal end 38. An elongated mid-section 231 is formed to extend between proximal end 36 and distal end 38. Mid-section 231 includes a flat surface 240 and a curved surface 242. Distal end 38 of base 230 is similar to distal end 28 of base 30 wherein base 230 is formed to include two cutting edges 50 forming tear-drop shaped opening 51 extending through distal end 38 of base 230. Apertures 52 are formed to extend through distal end 38 and are provided for receiving first pin 24 in order to pivotally couple tip 234 with base 230. Proximal end 36 of base 230 is formed to include a cylindrical section 250 having a hollow portion 252 extending therethrough. Mid-section 231 also includes a cut-out portion 254, as shown in FIG. 9. Shaft 20 of instrument 210 is received within hollow portion 252 of base 230 similar to the manner in which shaft 20 is received within shaft-receiving aperture 47 of base 30. Base 230 operates in the same manner as base 30.

Slider 232, as shown in FIG. 10 is formed to include a distal end 260, a proximal end 262 and an elongated mid-section 264 extending between distal end 260 and proximal end 262. Mid-section 264 is formed to include a flat surface 266 an a curved surface 268 so that when cutter 212 is assembled, flat surface 266 of slider 232 is adjacent to and engaged with flat surface 240 of base 230, as shown in FIG. 8. Distal end 260 is formed to include a rectangular shaped opening 270 and apertures 272 extending through distal end 260 and provided for receiving second pin 25 in order to pivotally coupled tip 34 with slider 232. Flat surface 240 of proximal end 262 of slider 232 is formed to include a groove 274 forming a stop-surface 276. Groove 274 is formed to receive rod 22 therein so that an upper surface (not shown) of rod 22 engages stop-surface 276. Slider 232 operates in the same manner as slider 32. During operation, slider 232 is urged upward by rod 22. Opening 270 is provided to allow tissue cut from the surgical site to pass therethrough. In the fully opened position, as shown in FIG. 8, a bottom surface 280 of slider 232 is positioned to rest on an upper surface 282 of cylindrical section 250.

Handle 216 is formed to operate the same as handle 16 of instrument 10. However, a left handle grip 294 and a right handle grip 296 are provided to include a ridged portion 315 on curved outer surface 110. Similar to splined portion 115, ridged portion 315 is provided to make handle 216 easy for user 116 to grasp. Like reference numbers to instrument 10 which are shown in FIGS. 8–10 are provided to denote the same members previously discussed as discussed in reference to instrument 10. Handle 216 also includes two rivets 298 shown at proximal end 18. Rivets 298 are provided in order to couple handle grips 294, 296 with center beam 97. The operation of instrument 210 is similar to the operation of instrument 10 whereby squeezing handle grips 294, 296 inward in direction 132, rod 22 is urged to move upward within shaft 20. Rod 22 thus urges slider 232 upward in order to pivot tip 34 so that cutter 212 may move from the fully opened position to the fully closed position.

Surgical instruments 10, 210 are used in minimally invasive endoscopic transitional space surgeries, although either instrument 10, 210 may be used in a variety of surgeries requiring the use of a type of cutter. An initial process in most minimally invasive endoscopic transitional space surgeries is cutting an uncinate process (not shown) for the purpose of exposing an ostium (not shown), which leads into a maxillary sinus cavity (not shown) within each patient's sinuses. Either surgical instrument 10, 210 of the present invention is inserted (usually in the fully closed position) into the nasal or sinus cavity of the patient. As mentioned previously, handle 16, 216 is held by user 116 with a pencil-like grip, which is illustrated in FIG. 7. Using the pencil-like grip, surgical instrument 10, 210 may be held as shown in FIG. 7, or surgical instrument 10, 210 may be held in the same manner but rotated 180 degrees about shaft 20. Surgical instrument 10, 210 is inserted in the fully closed position in order to prevent cutter head 74 from catching on any sinus tissues.

Once cutter head 74 is inserted past the ostium, user 116 allows surgical instrument 10, 210 to move to the normally biased, fully open position. The surgeon or user 116 then positions surgical instrument 10, 210 so that lower surface 75 faces toward and is generally parallel with the uncinate process to be cut. Once, tip 34 is hooked just behind the uncinate process, user 116 squeezes handle grips 94, 96 or handle grips 294, 196 toward center beam 97 in a tweezer-like fashion so that cutter 12, 212 is urged to move again to the fully closed position in order to cut the uncinate process and thereby open the ostium into the maxillary sinus cavity. Although the preferred use and operation of surgical instrument 10, 210 is described above, it is within the scope of the invention to include many uses and modes of operation for surgical instrument 10, 210.

Although the invention has been described in detail with reference to certain preferred embodiments, variations and modifications exist within the scope and spirit of the invention as described and defined in the following claims.

What is claimed is:

1. A surgical instrument adapted to be held by the thumb and index finger, supported on the middle finger and actuated by squeezing the thumb and index finger together, the surgical instrument comprising
    a shaft having a distal and a proximal end,
    a rod movable relative to the shaft,
    a cutting jaw including a pivoting cutter blade having two curved cutting edges,
    wherein the cutter blade is tear-drop shaped with side surfaces recessed from its two curved cutting edges,
    a base coupled to the cutter blade, and having two corresponding curved cutting edges forming an opening for receiving the cutter blade therein,
    wherein the cutting jaw is pivotally connected to the base and is pivotally connected to the rod for movement thereby relative to the base,
    a handle including two handle grips and a center beam and wherein the center beam is fixedly connected to the shaft, wherein each said handle grip is formed to be moved between an open position in which a distal end of each handle grip is spaced apart from the center beam and a closed position in which the distal end of each handle grip is adjacent the center beam, and
    wherein movement to the closed position causes the rod to move away from the proximal end of the shaft to cause the cutter blade to rotate backwards such that cutter blade pivots toward the shaft's proximal end to bring the cutting edges together.

2. The instrument of claim 1, wherein the handle grips are formed to include an outer curved surface having a ridged portion.

3. The instrument of claim 1, wherein the shaft is hollow and the rod is formed to be received within the shaft.

4. The instrument of claim 1, wherein the cutting jaw is further formed to include a slider coupled to the rod.

5. The instrument of claim 4, wherein the slider is formed to include an opening for receiving cut tissue therethrough.

6. The instrument of claim 5, wherein the opening of the slider and the opening of the base are positioned to align with each other when the handle is in the closed position.

7. The instrument of claim 4, wherein the cutter blade is coupled to the base at a first pivot point and is coupled to the slider at a second pivot point and also wherein the second pivot point is positioned to lie generally below the first pivot point when the handle is in the open position.

8. The instrument of claim 1, wherein the shaft and base remain stationary relative to the rod and cutter blade when the handle is being moved from the open position to the closed position.

9. The surgical instrument of claim 1 wherein the curved edges of the blade come to a point and wherein the underside of the blade is provided with a recess to permit the point to come into contact with the cutting edges on the base prior to other portions of the curve.

10. The surgical instrument of claim 1 wherein the cutting jaw is moveable over an angle of more than 90°.

* * * * *